United States Patent [19]

D'Angelo et al.

[11] Patent Number: 5,756,117
[45] Date of Patent: May 26, 1998

[54] MULTIDOSE TRANSDERMAL DRUG DELIVERY SYSTEM

[75] Inventors: Joseph P. D'Angelo; Henry Schur, both of Miami, Fla.

[73] Assignee: International Medical Asscociates, Inc., Miami, Fla.

[21] Appl. No.: 927,837

[22] Filed: Aug. 10, 1992

Related U.S. Application Data

[63] Continuation-in-part of Ser. No. 865,309, Apr. 8, 1992, abandoned.

[51] Int. Cl.$^6$ .................................................. A61F 13/00
[52] U.S. Cl. .......................... 424/449; 424/448; 602/41; 602/43; 602/52; 602/54; 602/57
[58] Field of Search ........................ 424/449, 448; 602/41, 43, 52, 54, 57, 58, 63, 901

[56] References Cited

U.S. PATENT DOCUMENTS

| | | | |
|---|---|---|---|
| 3,161,602 | 12/1964 | Herbig et al. | 252/316 |
| 3,270,100 | 8/1966 | Jolkouski et al. | 264/4 |
| 3,336,155 | 8/1967 | Rowe | 117/100 |
| 3,341,466 | 9/1967 | Brynko et al. | 252/316 |
| 3,396,117 | 8/1968 | Schatze | 252/188 |
| 3,405,070 | 10/1968 | Zolla | 252/316 |
| 3,567,650 | 3/1971 | Bakan | 252/316 |
| 3,797,494 | 3/1974 | Zattaroni | 128/260 |
| 3,875,074 | 4/1975 | Vassiliades et al. | 252/316 |
| 4,145,184 | 3/1979 | Brain et al. | 8/137 |
| 4,207,315 | 6/1980 | Voorhees | 424/200 |
| 4,277,364 | 7/1981 | Shasha et al. | 504/250 |
| 4,391,909 | 7/1983 | Lim | 435/178 |
| 4,422,970 | 12/1983 | Rajadhyaksha | 260/239.3 R |
| 4,460,368 | 7/1984 | Allison | 424/449 |
| 4,666,441 | 5/1987 | Androla et al. | 604/897 |
| 4,708,716 | 11/1987 | Sibalis | 604/20 |
| 4,743,249 | 5/1988 | Loveland | 424/447 |
| 4,806,355 | 2/1989 | Goosen et al. | 424/424 |
| 4,834,978 | 5/1989 | Nuwayset | 424/448 |

(List continued on next page.)

OTHER PUBLICATIONS

"Aminoguanidine, a Novel Inhibitor of Nitric Oxide Formation, Prevents Diabetic Vascular Dysfunction" Corbett et al, Diabetes, vol. 7, Apr. 1992, pp. 552–556.

Effect of Aminoguanidine on Functional and Structural Abnormalities in Peripheral Neive of STZ–Induced Diabetic Rates Yagihashi et al, Diabetes, vol. 41, Jan. 1992, pp. 47–52.

"Transdermal Delivery of Drugs" R. Vaidyanathan et al, vol. 2, pp. 63–83, 1990.

"Wirkung Peroraler und Transdermaler Insulin–Präparationen auf Blutglukose—Konzentiationen bei Mausen" Biedtke et al., Arnzeim.–Forsch./Drug Res. 40, No. 8 1990 pp. 880–883.

Transdermale Applikation vor Insulin ber TypII–Dia–Betiken, Liedtke et al., Drug Res. 40, No. 8, 1990, pp. 884–887.

Mechanistic Studies of Advanced Glycosylation End Product Inhibition by Aminoguanidine Diane Edelstein et al., Diabetes, vol. 41, Jan. 1992, pp. 26–29.

Retardation by Aminoguanidine of Development of Albuminura, Mesangial Expansion, and Tissue Fluorescene in Streptozocin—Induced Diabetic Rat, Soulis–Liparofa et al, Diabetes, vol. 40, Oct. 1991, pp. 1328–1334.

*Primary Examiner*—D. Gabrielle Phelan
*Attorney, Agent, or Firm*—Herbert L. Lerner; Laurence A. Greenberg

[57] ABSTRACT

A multidose transdermal drug delivery system comprises a laminate composite with a plurality of compartments. Each compartment is a reservoir for a unit dose of a drug active to be transdermally administered. The assembly is adhesively secured to the skin of a patient. Individual seals are provided for resealably enclosing the drug active in each of the reservoirs. The individual enclosing seals are removable to release the unit dose into contact with the skin of the patient and are actuable to control the transdermal absorption of the drug actives. Provisions are also made to automatically indicate the activation of the drug and to prevent an accidental release of medicament.

21 Claims, 5 Drawing Sheets

U.S. PATENT DOCUMENTS

| | | | |
|---|---|---|---|
| 4,904,475 | 2/1990 | Gale | 424/449 |
| 4,913,905 | 4/1990 | Fankhauser et al. | 424/449 |
| 4,917,676 | 4/1990 | Heiber et al. | 424/449 |
| 4,917,688 | 4/1990 | Nelson | 604/306 |
| 5,028,435 | 7/1991 | Katz et al. | 424/484 |
| 5,032,403 | 7/1991 | Sinnteich | 424/448 |
| 5,042,975 | 8/1991 | Chien et al. | 604/20 |
| 5,064,422 | 11/1991 | Wick | 604/307 |
| 5,064,654 | 11/1991 | Berner et al. | 424/448 |
| 5,071,704 | 12/1991 | Fischel-Ghodsian | 428/354 |

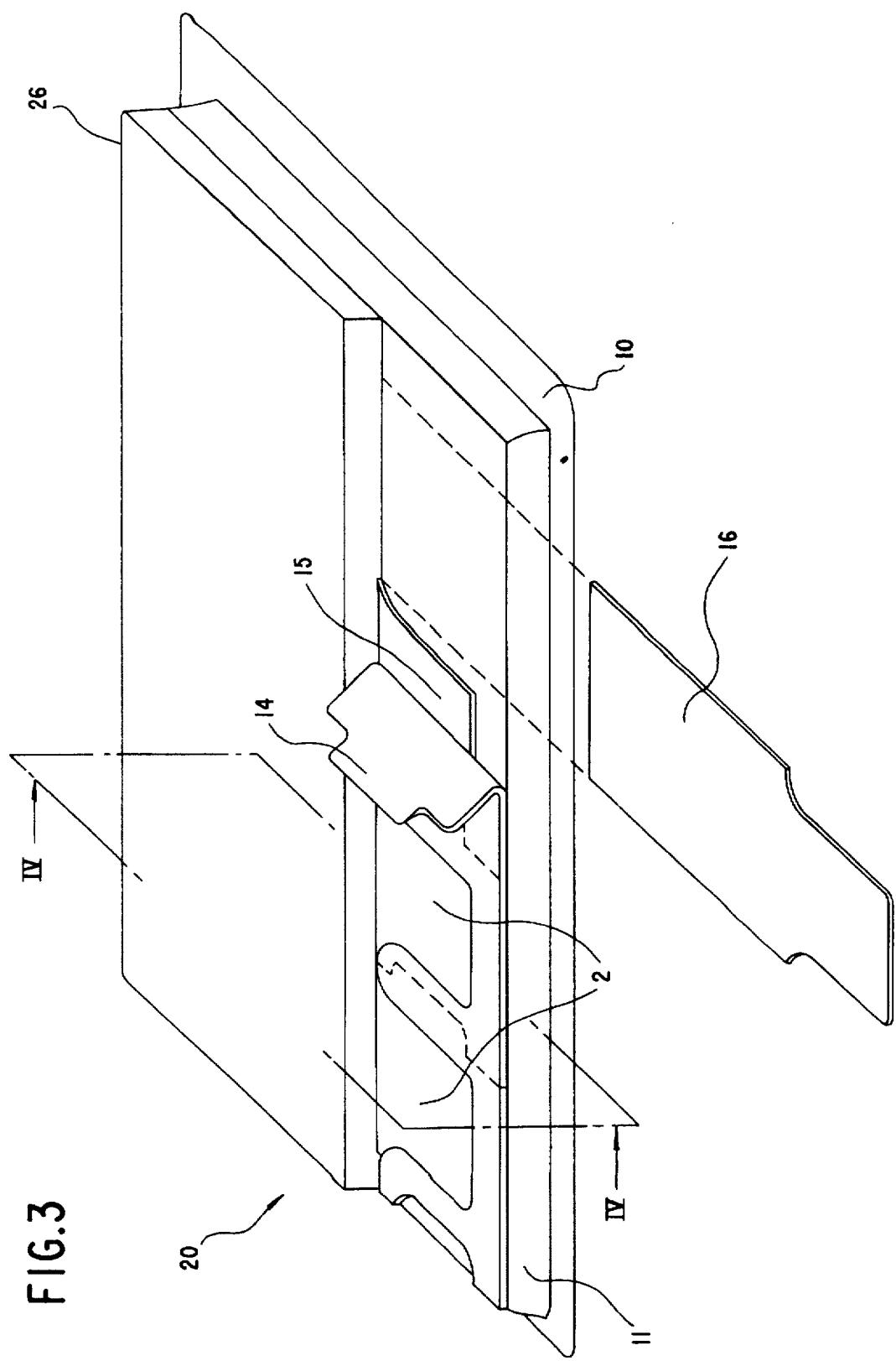

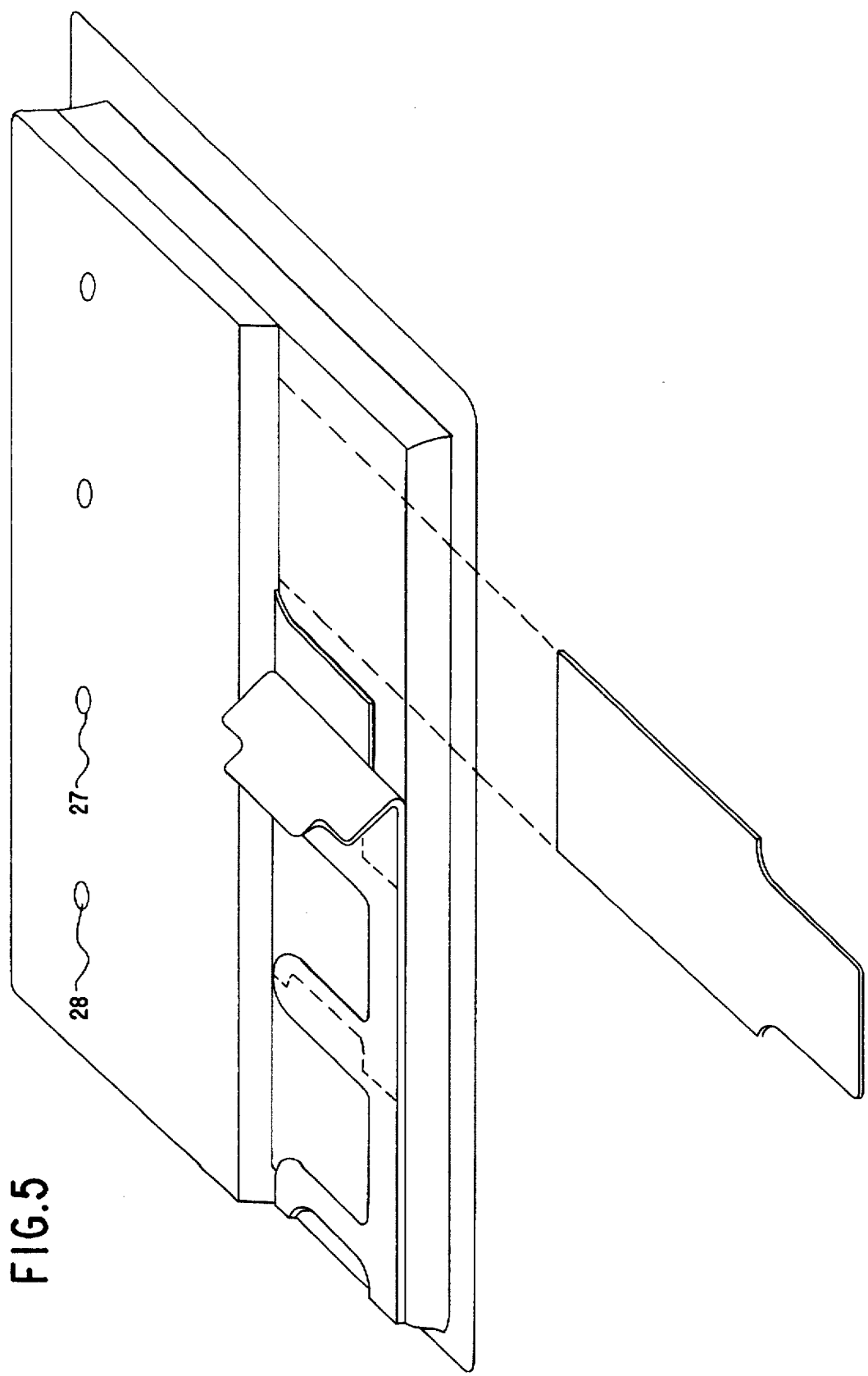

1

MULTIDOSE TRANSDERMAL DRUG DELIVERY SYSTEM

CROSS-REFERENCE TO RELATED APPLICATION

This application is a continuation-in-part of application Ser. No. 865,309, filed Apr. 8, 1992, now abandoned.

BACKGROUND OF THE INVENTION

1. Field of the Invention

This invention relates to transdermal medication assemblies and more particularly to such assemblies comprising multiple unit-dose reservoirs with each reservoir having individual tear-and-release or pull-and-release resealable closure means for initiation and administration of the medication.

2. Description of the Related Art

Transdermal drug administration has recently come to the forefront as a useful route for continuous dosing of useful drugs where other means of administration are either discontinuous, labor intensive or where other routes present absorption or inactivation problems. Whereas per os administration has been time honored i.e. "a teaspoonful three times a day", such unit dose administration was subject to erratic blood levels of the actives due to non-uniform absorption from the gut due to other gut contents or inactivation of the drug actives by the digestion process or the normal action of the liver. In addition, the need for active periodic administration i.e. three times a day, required active and willing participation by the patient or in home or hospital settings by the caregiver i.e. mother or nurse.

All these shortcomings are obviated by transdermal application where possible, of the drugs. A patch is adhered to a clear area of the skin and the drug is continually absorbed through the skin into the bloodstream for systemic distribution.

The skin is particularly useful as it presents large areas for drug administration, as the skin is the largest organ of the body. The utility of such a mode of administration has been promoted with the discovery and development of a group of compounds that promote transdermal penetration of the various active drugs. Such compounds are known in the art as penetration enhancers. They are generally characterized to be from the group of monovalent branched or unbranched aliphatic, cycloaliphatic or aromatic alcohols of 4–12 carbon atoms; cycloaliphatic or aromatic aldehydes or ketones of 4–10 carbon atoms, cycloalkanoyl amides of C 10–20 carbons, aliphatic, cycloaliphatic and aromatic esters, N, N-di-lower alkylsulfoxides, unsaturated oils, terpenes and glycol silicates.

These compounds and their specific activity as penetration enhancers, are more fully discussed in the text "Transdermal delivery of Drugs", A. F. Kydonie US (Dd)-1987 CRL Press and in such U.S. Pat. Nos. 4,913,905, 4,917,676 and 5,032,403.

As a result of these penetration enhancers, almost any drug, to some degree, can be administrated transdermally cf. U.S. Pat. Nos. 4,917,676, 3,598,122; 3,598,123; 3,742,951; 3,797,494; 3,948,254; 3,996,734; 4,284,444; and 4,597,961. Examples of such pharmacological actives include administration of antibacterial such as the penicillins, tetracyclines, second and third generation cephalosporins, chlor-amphenicol sulfonamides; sedatives and/or hypnotics, such as barbiturates, carbromal, antijussives such as codeine and dextromethorphan; anti-anxiety drugs such as the benzodiazepines including diazepam, buspirone; psychostimulants such as imipramine amitriptyline and other tricyclic anti-depressants; anti psychotic drugs and tranquilizers such as lithium, chlorpromazine and haloperidol, reserpine, thiopro-pazate; Parkinsonism control agents such as bromotriptine, percolide, the anticholmergics including benzotropine, pro-cyclidine, amantadine (also an antiviral); hormones and hormone antagonists and agonists, including adrenocortico-steroids; insulin, androgenic steroids, estrogenic and pro-gestrogenic steroids, thyroxin and its agonist 5-FU(fluoro-uracil), tamoxifen; antipyretics and analgesics such as aspirin/acetaminophen and other non-steroidal anti-inflammatory drugs (NSAID), analgesics based on morphine; morphine antagonists; vasodilating agents such as nitro-glycerine, isorbide dinitrate; alpha beta-blockers and other cardioactive drugs; antimalarials; anti-histamines and anti-cholinergics including atropine hyoscyamine or methscopalo-mine (for motion sickness; weaning agents such as nicotine for addiction to tobacco; and antiasthmatic bronchodilators such as formoterol; and combinations of such pharmaceutical actives.

Of course, while feasible, not all of these actives have yet been completely tested for efficacy by transdermal administration but many are under vigorous scrutiny. Other actives at this time are not economically viable for such administration, as the cost of full safety testing is too great for the specific number of patients involved.

As can be seen from this background discussion and the history of this type of medication, it is apparent that application by transdermal patch is a useful form for the administration of medication. However, a single dose per patch requires uneconomical repeated application.

SUMMARY OF THE INVENTION

It is an object of this invention to provide a multiple unit-dose transdermal patch assembly.

It is a further object of this invention to provide each unit dose in the multiple dose patch with an indicating means, visual or olfactory to inform the wearer or attendant concerning the activation for administration of each unit dose in the multidose patch assembly.

It is another object where a single application steady state dosing may not serve the best needs of the patient and be inconsistent with accepted clinical practice to provide a method of multiple sequential dosing in those cases. Additionally, this invention allows for the variation where needed in dose levels within a single "patch".

A further object is to provide a patch which is secured against accidental release of the medicament. This object is attained by providing a security strip.

Yet a further object of the invention is to provide a patch which may readily be refilled or the medication of which may be varied by insertion of medicament through a filling septum.

The patch assembly consists of a base in which the steady state dosage is or may be contained as needed by the patient and individual medicament reservoirs which may be activated by either a "tear-and-release" or "pull-and-release" mechanism. The reservoirs contain medicament which can be the same as contained in the base or various unit dosages of the base or entirely different synergistic medicaments.

Further objects and ancillary benefits will be apparent from the disclosure of the invention which comprises a multiple unit-dose transdermal drug delivery system or patch assembly. This invention includes the various drugs that can be delivered in unit doses, configurations of such assemblies, storage of the drugs within the assembly and includes delivery systems for the drugs from storage areas in the assembly to the skin, various systems for activating each unit-dose of the assembly, various means for indication activation of each unit-dose, various means to assure that the dosages are only delivered upon command and demand by the patient and to prevent accidental release and various means for insertion of medicament through a filling septum.

With the foregoing objects of the invention in view there is provided, in accordance with the claimed invention, a multidose transdermal drug delivery assembly, comprising a laminate composite of a drug-permeable membrane to be placed in contact with a patient's skin; a diffusable matrix such as a transfer gel layer disposed on the membrane; a permeable membrane disposed on the transfer gel layer; overlaid impervious drug enclosure means for receiving and protectively enclosing a drug active to be transdermally administered; the drug enclosure means and the permeable membrane defining a plurality of compartments therebetween defining reservoirs for respective unit doses of the drug active; and individual activation means for releasing unit doses of the drug active from respective ones of the compartments for contacting with the patient's skin.

In accordance with added features of the invention, assembly includes means for enclosing the drug active in each of the reservoirs.

In accordance with a further feature of the invention, the assembly includes actuating means for controlling transdermal absorption of the drug active and means for adhesively securing the laminate composite to the patient's skin.

In accordance with an additional feature of the invention, the reservoirs have a periphery which is smaller than a periphery of the permeable membrane and a periphery of the overlaid impervious layer, so that the permeable membrane and the overlaid impervious layer extend outwardly of the reservoir periphery.

In accordance with a further feature of the invention, the enclosing means are individual resealable strips disposed on the reservoirs for activating respective unit doses by peeling back respective ones of the strips. Also, the enclosing means may be individual sealing strips disposed between the reservoirs and the permeable membrane, the strips being removable from the assembly through a resealing strip for activating respective unit doses.

In accordance with yet additional features of the invention, the system includes means for indicating initiation of administration of a unit dose from a respective reservoir upon activation, which may be visual of olfactory signal means.

In accordance with yet a further feature of the invention, the reservoirs comprise microencapsulations of the drug active, the drug active may be insulin encapsulated into capsules of substantially 1 to 150 microns diameter, the microencapsulations are formed of a layer of polymer encapsulating the drug active, the polymer layer having drug-penetration moieties engrafted thereon; the moiety can be laurocapram; 1-dodecylhexahydro-2H-azepin-2-one.

In accordance with again an added feature of the invention, the transfer gel includes medicament for steady state dosage transdermal delivery.

In accordance with again a further feature of the invention, the assembly includes a plurality of security strips disposed above each of the individual activation means for preventing accidental activation of the drug active.

In accordance with again an additional feature of the invention, the compartments have openings in the form of fill ports formed therein for allowing introducing or withdrawing medicament from the reservoirs, and including a sealing filling septum closing the fill ports.

With the objects of the invention in view, there is further provided, a multidose transdermal drug delivery assembly, comprising a laminate composite having a plurality of reservoirs formed therein, unit doses with transdermal drug actives disposed in respective ones of the reservoirs for transdermal administration, individual seal means for enclosing the drug in each of the reservoirs, the unit doses being in the form of a multiphase composition of microspheres wherein an internal phase comprises the drug actives and adjuvants surrounded by an outer phase of film-forming polysaccarides engrafted with transdermal promoters, the microspheres being distributed through a diffusable matrix for the composition; the individual seal means having means for disrupting the microspheres upon activation of the seal means to release the drug actives and adjuvants in the unit dose compartment to diffuse through the matrix to a patient's skin. The laminate composite may include means for adhesively securing to a patient's skin.

In accordance with a concomitant feature of the invention, the assembly includes indicating means being freed by the seal means for signalling initiation and administration of the unit dose from each individual reservoir, and means for preventing accidental release of medicament.

In other words, the drug delivery assembly of this invention comprises a laminate composite having therein a series of at least two compartments, each compartment being a reservoir for a unit-dose of the drug-actives to be transdermally administered, adhesive means for adhering the support with the open face of the reservoir containing the drug actives being juxtaposed to the skin. Individual resealable closure means are provided containing the drug actives within the reservoir.

The resealable closure means on each unit dose reservoir are preferably provided with indicia for indicating that the unit dose has been released for administration. Among such indicia useful for indication of actuation and initiation of release of the unit dose, are colored stains or olfactory substances such as perfumes released upon actuation of the unit dose seal.

The laminate composite forming reservoirs for the drug actives and associated vehicles may be formed from flexible or rigid materials. Useful impervious materials include fabrics impregnated with film rendering the fabrics impervious to the drugs and vehicles, regenerated cellulose (cellophane), ABS polymer/cellulose acetate, ethyl cellulose, copolymers of plasticized vinylacetate-vinylchloride, polyethylene terephthlate; polyethylene, polypropylene, nylon film or nylon fabric impregnated with drug impervious films, polyvinylidene chloride, impregnated and coated papers and metallic foils, metalized shaped films of PVC, ABS and other shapeable polymeric sheets or films. The unit dose reservoirs of the assembly may be impressed or molded into the polymeric and impregnated materials or they may be formed by sealing the peripheries of impervious material layers to form pouches which, upon loading through openings, will become drug reservoirs. Useful dimensions for the patch are approximately one inch by two inches and up to about one quarter to half inch in thickness. The size of each reservoir is determined by the volume of the unit dose to be administered. The volumes exemplified are sufficient for most unit doses for transdermal delivery of the drugs, but larger or smaller volumes may be used. The drugs and their adjurants are dissolved, suspended, absorbed or contained in matrices or solutions. Useful matrices are gels of bipolymers i.e. alginates, gelatins, chitin, PVP, etc..

While the examples above disclose rectangular reservoirs, as they permit adjacent positioning of individual unit doses in a multiple dose assembly, the reservoirs in pouch or container form may also be circular, oval or irregular in form depending on positioning of the assembly on the body or limbs. Configuration of the assembly is dictated by the ultimate positioning of the assembly in areas where adhesion, absorption, and contact with clothes, limbs and body hair are to be taken into account.

The number of unit doses included in each assembly depends on the size of the reservoirs to configure a convenient size. Generally, four to ten unit doses are convenient with seven units preferred as permitting a single application of the drug once a day, or several times a day depending on the medicament and clinical application.

The principle of single unit doses in the multiple dose assembly is particularly useful as only a limited amount of the drug actives is exposed to the skin for transdermal absorption. When non-segregated multiple doses, as taught by the prior art are used, there arise problems.

A variant reservoir, which is a novel aspect of this invention consists of the micro encapsulation of the drug actives in a biopolymer to protect the drug from ambient degradation as well as to serve as a reservoir for the dosage volume. Insulin is an example of such a drug active. A specific advantage for the encapsulation of the drug in such a polymer is that it allows for the controlled rate of release of the medicament by adjustment of the crosslinking, density and specific type of polymer selected for the encapsulation.

In addition, passage of the relatively large molecule of the exemplified insulin as well as other hormone enzymes and proteins through the skin has been found to require some method of penetration enhancement. Several chemicals alone or in combination with certain solvents have been noted to promote transdermal penetration. It has been suggested that some of these materials perform their penetration by enlarging the intersticial spaces between the cells of the dermis. Such penetration vehicles or enhancers are known to the art and many are mentioned in the "Transdermal Delivery of Drugs".

Suitable penetration enhancers (flux enhancers are preferably monovalent, saturated or unsaturated aliphatic, cycloaliphatic or aromatic alcohols having from 4 to 12 carbon atoms. e.g. n-hexanol or cyclohexanol, aliphatic, cycloaliphatic or aromatic hydrocarbons having from 5 to 12 carbon atoms, e.g. hexane, cyclohexane, isopropylbenzene and the like, cyclo-aliphatic or aromatic aldehydes and ketones having from 4 to 10 carbon atoms, such as cyclohexanone, acetamide, N,N-di-lower alkylacetamides such as N, N-dimethylacetamide or N, N-diethyl-acetamide, $C_{10}$–$C_{20}$-alkanoylamides, e.g. N, N-dimethyllauroylamide, 1-n-$C_{10}$–$C_{20}$-alkylazcycloheptan-2-one, e.g. 1-n-dodeclyazacycloheptan-2-one(Azone® laurocapram), or N-2-hydroxyethylacetamide, and known vehicles and/or penetration enhancers such as aliphatic, cycloaliphatic and aromatic esters N, N-di-lower alkylsulphoxides, unsaturated oils, halogenated or nitrated aliphatic or cyclo-aliphatic hydrocarbons, salicylates, polyalkylene glycol silicates, and mixtures thereof.

EXAMPLE

The preferred penetration enhancer for use with microencapsulated insulin is the aforementioned "Azone®" laurocapram or 1-n-dodecylazacycloheptan-2-one because, in addition to being compatible to concentrated insulin, it is a lipophylic material.

The microencapsulation of insulin is done at low temperature i.e. below about 40° C. The insulin is solubilized at the desired concentration in a normal buffered saline (0.9N NaCl) solution of sodium alginate. The final solution contains 95% insulin. The mixture is slowly stirred to ensure uniformity and the microcapsules are formed by the conventional ultrasonic spraying into a conventional suitable crosslinker. While other methods may be utilized, the ultrasonic dispersant method produces a very uniform and controlled sphere size in a short time. Microencapsulating crosslinkers for sodium alginate may be polycations or polyanions. A Chitosan solution, as crosslinker, will produce uniform hard shell porous microcapsules of 150 microns or less depending on ultrasound frequency during spraying. Other methods of drop formation may be employed as known in the art such as by gravity, drop tube or air sprays. The size of the microcapsules is less than 150 microns with various ranges 1 to 150 microns being used depending on desired concentrations of the drugs to be administered.

The techniques of microencapsulation have been disclosed in U.S. Pat. Nos.

| | | | |
|---|---|---|---|
| 3,161,602 | 3,270,100 | 3,341,466 | 3,396,117 |
| 3,405,070 | 3,567,650 | 3,875,074 | 4,145,184 |
| 4,277,364 | 4,391,909 | | |

They are incorporated herein by references.

The microcapsules after washing in saline and dewatering may be re-encapsulated to reinforce their strength by use of known hard shell systems using gelatin, methylmethacrylate, chitin etc. as used in the microencapsulating of inks and perfumes. However, before the re-encapsulation, the invention includes the engrafting to the microcapsule-forming biopolymer, the penetration enhancer moiety, particularly Azone®. The microcapsules are coupled to the Azone® by combining a polymer matrix of PUP and glycerine with the Azone® to a 1–10% polymer matrix and then reacting therewith by contact, the microcapsules under temperatures slightly above room temperatures. The "so-grafted" polymer matrix capsules are then overlaid to reinforce them or may be directly utilized by introduction into the reservoir.

Other dermal penetration of absorption enhancers may be added to a gel matrix in which the engrafted microcapsules are incorporated.

It is preferably a hydrogel through which the insulin can rapidly diffuse. The absorption enhancers include surface tension modifiers for the gel matrix as well as detergents for preparing the epidermis. Also useful for inclusion are typical vasodilators including the pharmaceutically acceptable vasolidator, physalemin.

The hydrogel matrix containing the microencapsulated insulin is introduced into commercially available transdermal single patch applicators or into the afore-mentioned multi-dose transdermal patch assembly for unit dose application.

In animal tests patches containing insulin microencapsulated as above, have been applied to the shaved skin of a series of insulin-deficient animals and the microcapsules have been disrupted to free the insulin into contact with the shaved skin. Within 30 minutes, all animals exhibited measurable insulin levels in the blood. By adjustment of insulin concentration in the microcapsules, therapeutic blood levels could be realized.

The commercial test patches mentioned above, are prepared using the drug impervious fabric for forming the pouch Scotchpak® Backing 12006, manufactured by 3M Corp.

The pouches were filled with the drug, hydrogel through major openings in the layer to be applied to the skin. The openings were covered with a permeable film of Cotran® 9710 (also 3M), a micro-porous polyethylene. The patch was adhered to the shaved skin by the 3M Cotran® 9872 acrylate adhesives approved for contact with the skin and commercially offered for transdermal patch adhesive. Other useful adhesives for adhering the patches to the skin are disclosed in U.S. Pat. No. 3,797,494.

In addition to the administration of insulin by transdermal application in the form of microcapsules, it is also useful to administer, transdermally, either from the same patch or reservoir or from an adjacent reservoir or compartment in the multiple assembly of this invention, an effective amount of aminoguanidine to inhibit diabetic retinopathy. This form of retinopathy is a serious complication of diabetes and is not completely countered by insulin alone.

This retinopathy results from advanced glycosylation end-products (AGEs) resulting from the improper metabolism caused by diabetes.

Aminoguanidine is an inhibitor of AGEs and has been shown by such inhibition, to mitigate the collagen crosslinking, caused by the AGEs, leading to the progressive ocular complications of diabetes.

The transdermal application of the aminoguanidine can be in the form of a gel-suspension of the aminoguanidine. It can also be introduced into the transdermal patches in frangible microcapsules in the manner described herein for insulin. The microcapsules of aminoguanidine may be transdermally administered either admixed with microcapsules of insulin in the same patch or patch reservoir or the aminoguanidine and the insulin may be admixed with the insulin prior to formation of the microcapsules.

It is also useful, under certain circumstances, to position the aminoguanidine matrix in a separate reservoir adjacent to the insulin-containing reservoir and either activating each reservoir separately or concurrently. The adjuvants useful for insulin are often also useful for the aminoguanidine.

BRIEF DESCRIPTION OF THE DRAWING

FIG. 3 is a perspective view of a second embodiment of a transdermal patch assembly according to the invention;

FIG. 5 is a view as in FIG. 3 showing filling ports and filling septa; and

DESCRIPTION OF THE DRAWING

Figure 1:
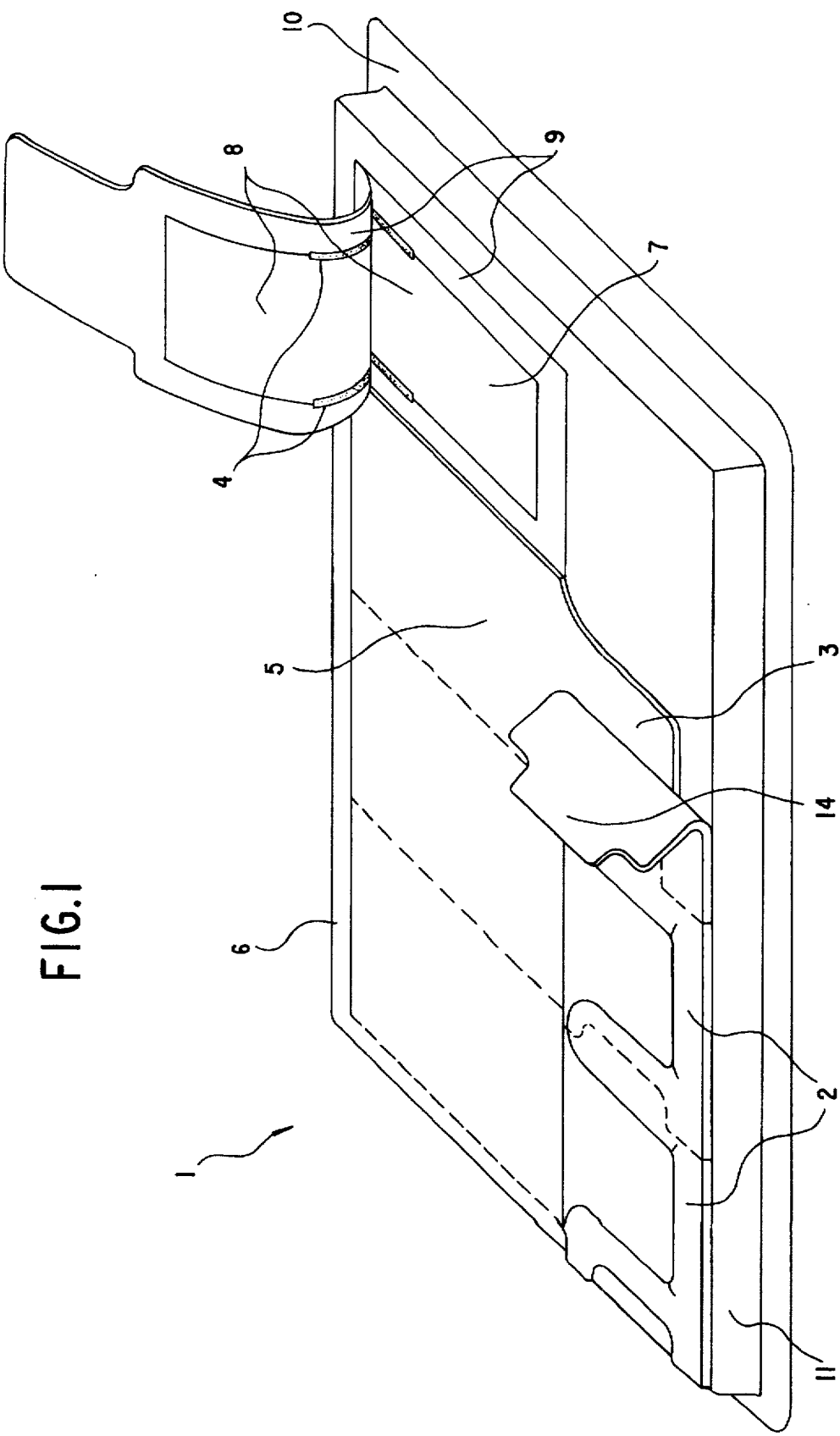
FIG. 1 is a perspective view of a first embodiment of a multidose transdermal patch assembly according to the invention.
Figure 2:
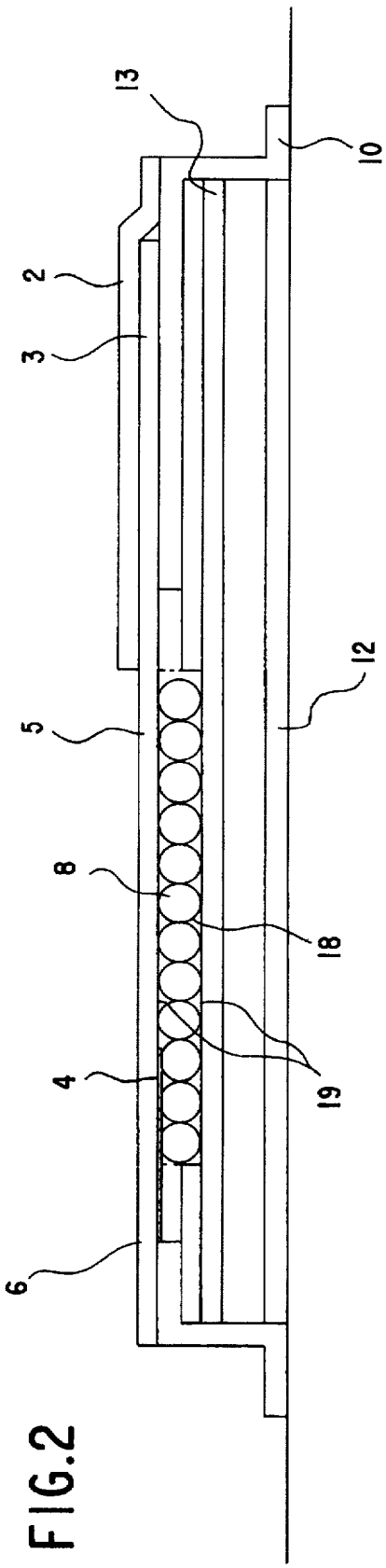
FIG. 2 is a cross-sectional view through the assembly of FIG. 1.

Referring now to the figures of the drawing in detail and first, particularly, to FIGS. 1 and 2 thereof, there is seen a multidose transdermal tear-and-release patch assembly 1, comprising a laminate composite of layers forming individual unit cells 7 with each cell containing a layer of microencapsulated medicament 8. The assembly is a plurality of individual unit dose cells 7 having impervious walls separating each cell 7, from its respectively adjacent cell. The unit cells 7 are filled with the desired medicament (drug actives) in microcapsule form 8. The unit cells 7 may also contain a gel-like matrix 18. The layer of microencapsulated medicament 8 is adhered to the bottom of a tear strip 5 and to the top of permeable membrane 13 by microcapsule adhesive 19.

The microencapsulated medicament 8 of each unit cell 7 may be identical or may be varied. The variation of the encapsulated medicament 8 may consist of differing strengths of the medicament which may be freed to the skin in response to variations in the clinical condition. It is also possible to provide in adjacent cells 7, differing medicaments, for example insulin in one and aminoguanidine in the other. These medicaments are related to the individual condition for which the patch is prescribed and thus, such a combination therapy is advantageous.

The unit dose cells 7 are closed to include the unit dose of encapsulated medicament 8 and gel matrix 18 by the overlaid tear strip 5 and the underlying permeable membrane 13. If necessary, the permeable membrane 13 may be utilized to control the rate of passage of encapsulated medicament 8 from the unit cell 7 into the diffusable matrix or transfer gel 11 after activation of the unit dose.

Each unit dose is activated by a two-step process. Step #1 is the removal of a security strip segment 2 by pulling back on a tab 14, which thereby exposes a tear-and-release tab 3. The purpose of the security strip 2 is to prevent any accidental release of the medicament. In step #2, each unit dose is individually activated by pulling up the tear and release tab 3 located on the end of each tear strip 5. When the tear strip 5 is pulled back to its attachment area 6, activation indicator 4 is released to provide the patient with a confirmation of the full activation of medicament 8. As the tear strip 5 is pulled back, the frangible medicament capsules are ruptured, thereby releasing the medicament 8, which diffuses through the permeable membrane 13, into the transfer gel 11 and through a patch/skin interface membrane 12 and is ready for absorption into the skin. The skin patch interface membrane 12 may be completely pervious to the contents of the cell. The transfer gel 11 may or may not contain a steady state medicament in appropriate dosage as required by the individual patient.

The tear strip 5 is secured to the unit dose 7 by an attachment area 6 where it is hinged at that point. In addition, it is adhered to the periphery of the unit dose 7 by a reservoir perimeter adhesive 9, which serves as the seal for unit dose 7. The tear strip 5 is provided with sufficient peripheral surface for reclosure of unit dose 7 by repositioning the tear strip 5 on the assembly 1 via reservoir perimeter adhesive 9.

The entire assembly is fastened to the skin by an adhesive border 10 which is adhesive coated to ensure positioning on the skin. The adhesive border 10 is preferably formulated to allow for repositioning of the assembly.

Figure 4:
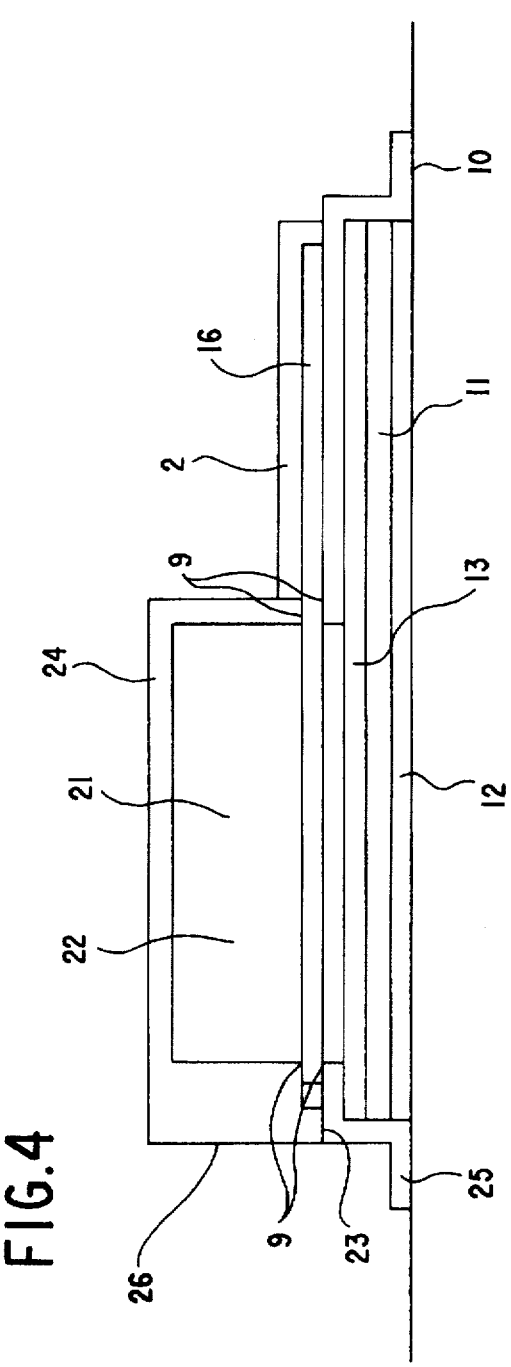
FIG. 4 is a cross-sectional view of the assembly of FIG. 3 along the plane IV—IV as seen in the direction of the arrows.

Referring to FIGS. 3 and 4 which show a multi unit dose transdermal pull pouch assembly 20, comprising a laminate composite of layers forming individual medicament drug wells 21 containing medicament 22 in a plurality of forms, including but not limited to liquid, gel, microencapsulation or gas. The assembly 20 defines a series or plurality of individual dose medicament wells 21 having impervious walls separating each medicament well from its adjacent well. The medicament within each well 21 may be identical or may be varied, as mentioned in the context of the embodiment of FIGS. 1 and 2. The pull pouch medicament 22 is closed within the medicament well 21 by an overlaid drug impervious support 24 and an underlying impervious pull pouch strip 16.

Each unit dose of medicament is activated by a two-step process, similar to that explained in the context of FIGS. 1 and 2. Step #1 is the removal of the security strip segment 2 by pulling back on its tab 14, which thereby exposes pull pouch tab 15. The purpose of the security strip is to prevent any accidental release of the medicament. In step #2 each unit dose is individually activated by pulling on pull pouch tab 15 until pull pouch strip 16 is removed from the assembly 20. Removal of the impervious pull pouch strip 16 allows the pull pouch medicament 22 to diffuse through the permeable membrane 13, into the transfer gel 11 and thru the patch/skin interface membrane 12 and is ready for absorption into the skin.

The pull pouch strip 16 is secured to assembly 20 at its posterior end 26 by adhesive 23. The posterior end 26 of the pull pouch strip 16 is perforated and will tear free from the pull pouch assembly 20 upon pulling on the pull pouch tab 15.

A basal attachment membrane 25 is disposed below the pull pouch strip 16, which membrane 25 has on its upper surface reservoir perimeter an adhesive 9. The adhesive extends from the perimeter of the medicament well 21 to the perimeter of the pull pouch strip 16. Above the pull pouch strip 16 is a drug impervious support 24 which has on its lower surface the reservoir perimeter adhesive 9, which adhesive extends from the perimeter of the medicament well 21 to the perimeter of the pull pouch strip 16. Above the pull pouch strip 16 is a drug-impervious support 24 which has on its lower surface the reservoir perimeter adhesive 9, which adhesive extends from the perimeter of medicament well 21 to the perimeter of the pull pouch strip 16. The upper and lower surfaces of the pull poutch strip 16, which come into contact with the reservoir perimeter adhesive 9 are made from a non-adhering material, thereby permitting the pull pouch strip 16 to be removed from the assembly 20 without affecting the adhesive which is above and below it. The pull pouch strip 16 is manufactured from a non-adhesive material. Upon removal of the pull pouch 16 from the assembly 20, the reservoir perimeter adhesive 9 on the surfaces of the basal attachment or occulatory membrane 25 and the drug impervious support 24 adhere to one another forming a complete seal and preventing any leakage of the medicament 22.

The basal attachment membrane 25 extends past the patch/skin interface membrane 12 providing a surface to attach the assembly 20 to the skin via the border adhesive to ensure positioning on the skin. The adhesive is preferably formulated to allow for repositioning of the assembly.

If the medicament well 21 contains medicament in the microencapsulated form, pulling the pull pouch strip 16 from the assembly will rupture the microcapsules, thereby releasing the medicament for diffusion to the skin.

The pull pouch strip 16 may contain indicators to show the release of medicament from the medicament well 21. Such indicators would alert the patient as to the activation state of the medicament within the individual dose unit of the assembly 20. Indicators may consist of pigments released from microcapsules as known in the art, olfactory signals similarly microencapsulated and released by removal of pull pouch strip 16 or visual indicators located on the pull pouch strip 16.

Figure 6:
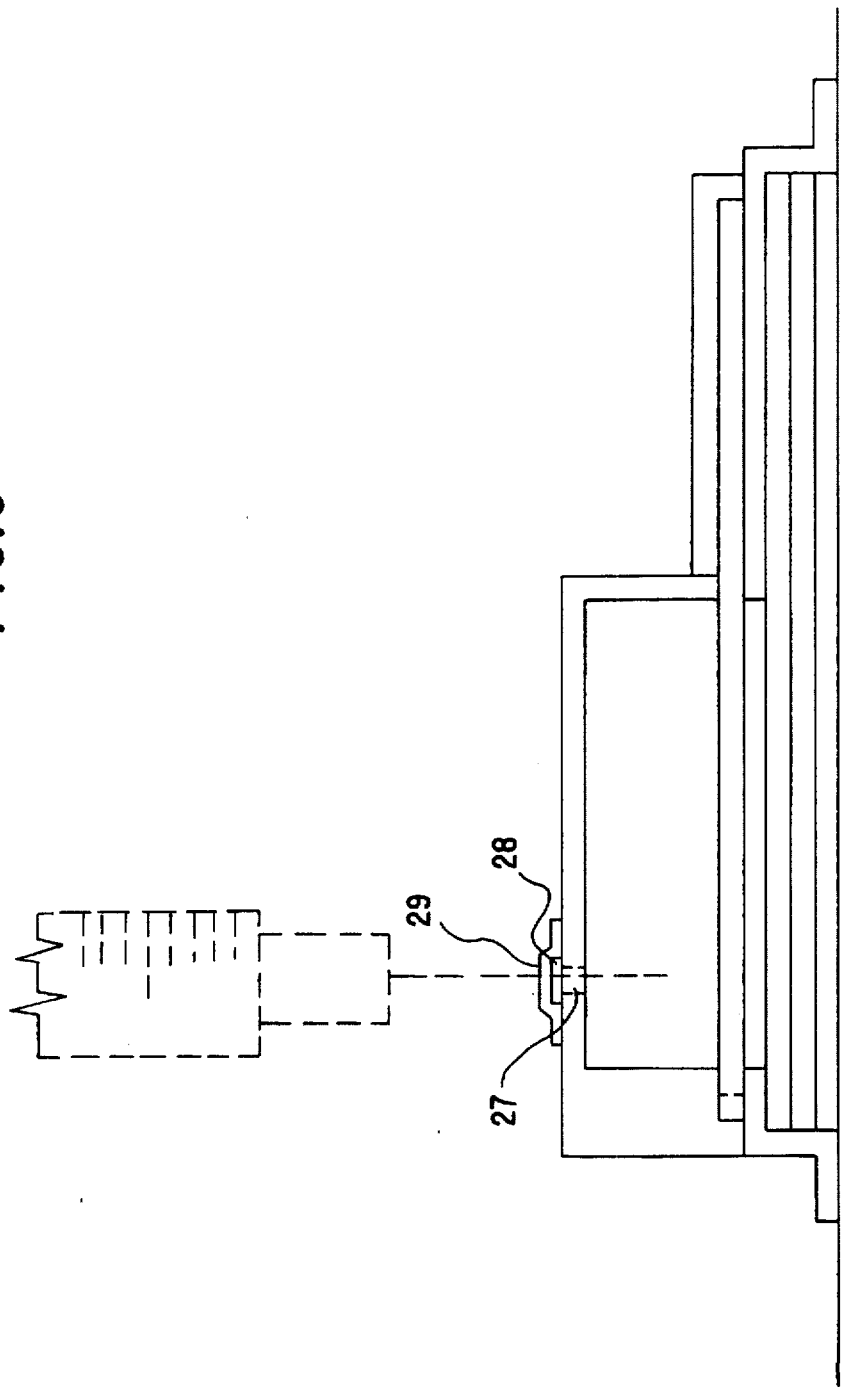
FIG. 6 is a view as in FIG. 4 showing a cross-section of the embodiment shown in FIG. 5 and additionally indicating a syringe for filling the medicament pouch through a fill port.

Referring to FIGS. 5 and 6, the uppermost composite layer of the pull pouch assembly 20 has a fill port hole 27, above each medicament well 21, into which is placed or fitted a filling septum which allows for the aseptic introduction or withdrawal of medicament into the medicament well 21. The preferred method for the introduction or withdrawal of medicament is by syringe and needle. The filling septum 28 provides both a method for the medicament to be introduced into the medicament well 21 and also self-seals and protects the medicament after it has been inserted. Individually covering each fill port 27 and filling septum 28 is a septum protector 29, which is to be removed prior to insertion of medicament. The medicament well 21 may or may not contain gel or other non-medicament or medicament components as required.

This assembly is advantageous as it allows for customizing of the medicament to meet specific clinical needs which will be obvious to those skilled in the healing arts.

We claim:

1. A multidose transdermal drug delivery assembly, comprising a laminate composite of a transfer gel layer;

a permeable membrane disposed on said transfer gel layer;

overlaid impervious drug enclosure means for receiving and protectively enclosing a drug active to be transdermally administered;

said drug enclosure means and said permeable membrane defining a plurality of compartments therebetween defining reservoirs for respective unit doses of the drug active;

individual activation means for releasing unit doses of the drug active from respective ones of said compartments for contacting with a patient's skin; and means for enclosing the drug active in each of said reservoirs, said enclosing means being individual resealable strips disposed on said reservoirs in a spaced-apart relationship with said transfer gel layer for activating respective unit doses by peeling back respective ones of said strips while said laminate composite is disposed on the patient's skin.

2. The assembly according to claim 1, including means for adhesively securing said laminate composite to the patient's skin.

3. The assembly according to claim 1, wherein said reservoirs have a periphery being smaller than a periphery of said permeable membrane and a periphery of said overlaid impervious layer, so that said permeable membrane and said overlaid impervious layer extend outwardly of said reservoir periphery.

4. A multidose transdermal drug delivery assembly, comprising a laminate composite of a transfer gel layer;

a permeable membrane disposed on said transfer gel layer;

overlaid impervious drug enclosure means for receiving and protectively enclosing a drug active to be transdermally administered;

said drug enclosure means and said permeable membrane defining a plurality of compartments therebetween defining reservoirs for respective unit doses of the drug active;

individual activation means for releasing unit doses of the drug active from respective ones of said compartments for contacting with a patient's skin; and means for enclosing the drug active in each of said reservoirs, said enclosing means being individual sealing strips disposed between said reservoirs and said permeable membrane, said strips being removable from said assembly through a resealing strip for activating respective unit doses while said laminate composite is disposed on the patient's skin.

5. The assembly according to claim 1, including means for indicating initiation of administration of a unit dose from a respective reservoir upon activation.

6. The assembly according to claim 5, wherein said indicating means are visual signal means.

7. The assembly according to claim 5, wherein said indicating means are an olfactory signal means.

8. The assembly according to claim 1, wherein said reservoirs comprises microencapsulations of the drug active.

9. The assembly according to claim 8, wherein the drug active is insulin encapsulated into capsules of substantially 1 to 150 microns diameter.

10. The assembly according to claim 8, wherein the microencapsulations are formed of a layer of polymer encapsulating the drug active, said polymer layer having drug-penetration moieties engrafted thereon.

11. The assembly according to claim 10, wherein said moiety is laurocapram; 1-dodecylhexahydro-2H-azepin-2-one.

12. The assembly according to claim 1, wherein said transfer gel includes medicament for steady state dosage transdermal delivery.

13. The assembly according to claim 1, including a plurality of security strips disposed above each of said individual activation means for preventing accidental activation of the drug active.

14. The assembly according to claim 1, wherein said compartments have openings in the form of fill ports formed therein for allowing introducing or withdrawing medicament from said reservoirs, and including a sealing filling septum closing said fill ports.

15. A multidose transdermal drug delivery assembly, comprising a laminate composite of a diffusible matrix;

a permeable membrane disposed on said diffusible matrix;

overlaid impervious drug enclosure means for receiving and protectively enclosing a drug active to be transdermally administered;

said drug enclosure means and said permeable membrane defining a plurality of compartments therebetween defining reservoirs for respective unit doses of the drug active;

individual activation means for releasing unit doses of the drug active from respective ones of said compartments for contacting with a patient's skin; and means for enclosing the drug active in each of said reservoirs, said enclosing means being individual resealable strips disposed on said reservoirs for activating respective unit doses by peeling back respective ones of said strips while said laminate composite is disposed on the patient's skin.

16. The delivery assembly according to claim 15, including a drug-permeable membrane to be placed in contact with a patient's skin disposed below said diffusible matrix.

17. A multidose transdermal drug delivery assembly, comprising a laminate composite of diffusible matrix means;

overlaid impervious drug enclosure means for receiving and protectively enclosing a drug active to be transdermally administered;

said drug enclosure means defining a plurality of compartments defining reservoirs for respective unit doses of the drug active;

individual activation means for releasing unit doses of the drug active from respective ones of said compartments for contacting with a patient's skin; and means for enclosing the drug active in each of said reservoirs, said enclosing means being individual sealing strips disposed between said reservoirs and said diffusible matrix, said strips being removable from said assembly through a resealing strip for activating respective unit doses while said laminate composite is disposed on the patient's skin.

18. The assembly according to claim 17, including means for adhesively securing said laminate composite to the patient's skin.

19. The assembly according to claim 17, wherein said reservoirs have a periphery being smaller than a periphery of said overlaid impervious layer, so that said overlaid impervious layer extends outwardly of said reservoir periphery.

20. The assembly according to claim 17, including means for indicating initiation of administration of a unit dose from a respective reservoir upon activation.

21. The assembly according to claim 17, wherein said reservoirs comprise microencapsulations of the drug active.

\* \* \* \* \*